(12) United States Patent
Olbrich et al.

(10) Patent No.: US 6,486,124 B2
(45) Date of Patent: Nov. 26, 2002

(54) CYCLOSPORIN COMPOSITIONS AND PROCESS THEREFOR

(75) Inventors: Matthias Olbrich, Reichenberg; Heinrich Potter, Radebeul, both of (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/981,929

(22) Filed: Oct. 17, 2001

(65) Prior Publication Data

US 2002/0025927 A1 Feb. 28, 2002

Related U.S. Application Data

(63) Continuation of application No. 09/605,512, filed on Jun. 28, 2000, now abandoned, which is a continuation of application No. 09/134,298, filed on Aug. 14, 1998, now abandoned, which is a continuation of application No. 08/806,106, filed on Feb. 25, 1997, now abandoned, which is a continuation-in-part of application No. PCT/DE95/00951, filed on Jul. 19, 1995.

(30) Foreign Application Priority Data

Nov. 3, 1994 (DE) .......................................... 44 38 861

(51) Int. Cl.$^7$ ............................................. A61K 38/13
(52) U.S. Cl. ......................................................... 514/11
(58) Field of Search ........................................... 514/11

(56) References Cited

U.S. PATENT DOCUMENTS

| | | | | |
|---|---|---|---|---|
| 3,288,824 A | 11/1966 | Mahler et al. | ............ | 260/410.6 |
| 3,813,345 A | 5/1974 | Urton | .......................... | 252/312 |
| 3,954,967 A | 5/1976 | Urton | .......................... | 424/78 |

(List continued on next page.)

FOREIGN PATENT DOCUMENTS

| | | |
|---|---|---|
| BE | 895724 | 7/1983 |
| CA | 1209361 | 8/1986 |
| CH | 2461786 | 6/1983 |
| CH | 8634788 | 6/1983 |
| CH | 641356 | 2/1984 |
| DE | 3315805 | 11/1984 |
| DE | 3924207 | 1/1990 |
| DE | 4418115 | 12/1994 |
| EP | 041795 | 12/1981 |
| EP | 135171 | 3/1985 |
| EP | 170623 | 2/1986 |
| EP | 211258 | 2/1987 |
| EP | 256856 | 2/1988 |
| EP | 274431 | 7/1988 |
| EP | 314689 | 5/1989 |
| EP | 0 315 079 | 5/1989 |
| EP | 361928 | 4/1990 |
| EP | 589843 | 3/1994 |
| EP | 650730 | 5/1995 |
| EP | 705601 | 4/1996 |
| FR | 2553661 | 4/1985 |
| FR | 2642650 | 8/1990 |
| FR | 2678169 | 12/1992 |
| GB | 1171125 | 11/1969 |
| GB | 2098865 | 12/1982 |
| GB | 2206119 | 12/1988 |
| GB | 2209671 | 5/1989 |
| GB | 2 211 408 | 7/1989 |
| GB | 2218334 | 11/1989 |
| GB | 2221848 | 12/1989 |
| GB | 2221157 | 1/1990 |
| GB | 2222770 | 3/1990 |
| GB | 2224205 | 5/1990 |
| GB | 2228198 | 8/1990 |
| GB | 2230440 | 10/1990 |
| JP | 1249918 | 4/1985 |
| JP | 249918 | 7/1986 |
| JP | 61280435 | 12/1986 |
| JP | 4049-232 | 6/1990 |
| WO | 86/02264 | 4/1986 |
| WO | 87/01035 | 2/1987 |
| WO | 88/00059 | 1/1988 |
| WO | 90/08537 | 8/1990 |
| WO | WO 91/12008 | 8/1991 |
| WO | WO 92/09299 | 6/1992 |
| WO | 93/20833 | 10/1993 |
| WO | WO 95/22982 | 8/1995 |
| WO | WO 96/14079 | 5/1996 |

OTHER PUBLICATIONS

95:225610K, Anon. (1981).
Anon., Research Disclosure 21143 (Nov. 1981), p. 420.
Beyer, et al., Pharmazie in unserer Zeit, vol. 12(2):55–60 (1983).
Bhargava, et al., Pharmaceutical Tejchnology, Mar., 1989, pp. 46–54.
Cavanak and Sucker, Prog. Allergy vol. 38:65–72 (1986).
Ekman, S., Lipids 22: 657–663 (1987).
Ritschel, et al., Pharmaceutical Research vol. 5(10): PD943 Suppl. 108 (1988).
Frazer, et al., J. Physiol. (1944) vol. 103, pp. 306–316.
Jayakrishnan, et al., J. Soc. Cosmet, Chem. 34:335–350 (1983).
Mizushima, 86–335072/51 (Apr. 26, 1985)—Abstract.
Mubarak, Development and Testing of New Microemulsions 1–51 (1982) (translation).

(List continued on next page.)

*Primary Examiner*—Phyllis G. Spivack
(74) *Attorney, Agent, or Firm*—Gabriel Lopez

(57) ABSTRACT

The invention relates to formulations of cyclosporin with high bioavailability for oral administration, which contain about 1 part by weight of one or more cyclosporin(s), preferably cyclosporin A and/or cyclosporin G, 7.5 to 7.8 parts by weight of one or more polyethylene glycol esters of saturated $C_{10}$–$C_{22}$hydroxy fatty acids, 0.7 to 0.85 part by weight of a monohydric alcohol as co-solvent, and 0.7 to 0.8 part by weight of a polyhydric alcohol as co-solvent. The drug form is produced by initially dissolving the cyclosporin in ethanol and, while stirring, adding propylene glycol and SOLUTOL® HS 15 until a clear, viscous solution results, bottled as drinkable solution or packed into capsules.

17 Claims, 1 Drawing Sheet

U.S. PATENT DOCUMENTS

| | | | | |
|---|---|---|---|---|
| 4,073,943 | A | 2/1978 | Wretlind et al. | 424/358 |
| 4,117,118 | A | 9/1978 | Härri et al. | 424/177 |
| 4,146,499 | A | 3/1979 | Rosano | 252/186 |
| 4,156,719 | A | 5/1979 | Sezaki et al. | 424/177 |
| 4,388,307 | A | 6/1983 | Cavanak | 424/177 |
| 4,567,161 | A | 1/1986 | Posanski et al. | 424/199 |
| 4,695,450 | A | 9/1987 | Bauer et al. | 424/168 |
| 4,719,239 | A | 1/1988 | Muller et al. | 514/785 |
| 4,794,000 | A | 12/1988 | Ecanow | 424/457 |
| 4,797,272 | A | 1/1989 | Linn et al. | 424/59 |
| 4,797,273 | A | 1/1989 | Linn et al. | 424/59 |
| 4,798,823 | A | 1/1989 | Witzel | 514/11 |
| 4,835,002 | A | 5/1989 | Wolf et al. | 426/590 |
| 4,888,239 | A | 12/1989 | Brox | 428/402.2 |
| 4,914,188 | A | 4/1990 | Dumont et al. | 530/317 |
| 4,963,367 | A | 10/1990 | Ecanow | 424/484 |
| 4,990,337 | A | 2/1991 | Kurihara et al. | 424/427 |
| 4,996,193 | A | 2/1991 | Hewitt et al. | 514/11 |
| 5,037,653 | A | 8/1991 | Dawson | 424/405 |
| 5,047,396 | A | 9/1991 | Orban et al. | 514/11 |
| 5,154,754 | A | 10/1992 | Damo et al. | 71/DIG. 1 |
| 5,177,110 | A | 1/1993 | Oechslein et al. | 514/594 |
| 5,206,219 | A | 4/1993 | Desai | 514/3 |
| 5,260,301 | A | 11/1993 | Nakanishi et al. | 514/291 |
| 5,338,761 | A | 8/1994 | Nakajima et al. | 514/772 |
| 5,342,625 | A | 8/1994 | Hauer | 424/455 |
| 5,525,590 | A | 6/1996 | Bollinger et al. | 514/11 |
| 5,639,724 | A | 6/1997 | Cavanak | 514/11 |
| 5,756,450 | A | 5/1998 | Hahn et al. | 514/9 |
| 5,759,997 | A | 6/1998 | Cavanak | 514/11 |

OTHER PUBLICATIONS

Muller, et al., Pharm. Ind. 50(11) 1301–1306 (1988) (translation).

Muller, et al., Pharm. Ind. 50(3): 370–375 (1988) (translation).

Pohler, Micro–Emulsion Gels Structural Investigations and Galenical Properties 1–100 (1983) (translation).

Remington's Pharmaceutical Sciences (17th ed.). Microemulsions, Chapter 20, pp. 293–300 (1985).

W.A. Ritschel, Methods and Findings in Experimental and Clinical Pharmacology, vol. 13, pp. 205–220 (1991).

Reymond, In Vitro In Vivo Model for the Absorption of Cyclosporin A (1988) Pharmaceutical Research, 5(10), pp. 677–679.

Ritschel, et al. Meth. and Find Exp. Clin. Pharmacol. vol. 11(4): 281–87 (1989).

Takada, et al., Intern'l Jour. of Pharmaceutics, vol. 44: 107–116 (1988).

Takada, et al., J. Pharmaceutical Research, vol. 3(1): 48–51 (1986).

Takada, et al., J. Pharmacobio–Dyn., vol. 11: 80–87 (1988).

Takada, et al., J. Pharmacobio–Dyn., vol. 8: 320–323 (1985).

Tarr, et al., Pharmaceutical Research, vol. 6(1): 40–43 (1989).

Yanagawa, et al., J. Microencapsulation 6(2): 161–164 (1989).

Ziegenmeyer, et al., Acta Pharmaceutical Technologica, vol. 26(4): 273–275, 1980 (translation).

Derwent Abst. 92/216,793/26 (1990).

The Merck Index, 9th Ed., Merck & Co. Inc., Rahway, N.J. p. 1017 (1976).

Derwent Abst. 84/069426/12 (1984).

Derwent Abst. 92/235168/29 (1989).

Derwent Abst. 92/216793/26 (1990).

Carrigan, et al., J. Pharm. Sci., 1973, vol. 62, pp. 1476–1479.

Coon et al., Cancer Res., vol. 51, No. 3, 897–902 (1991).

Board, P.G., FEBS Lett., vol. 315, No. 3, 298–300 (1993).

Froemming et al., Acta Pharm, Technol., vol. 36, No. 4, 214–220 (1990).

Kraus et al., Acta Pharm. Technol., vol. 36, No. 4, 221–225 (1990).

Perez, J.A., Farmacotecnia, 202–205 (1967).

Average relative bioavailability (AUC ± standard deviation) of I (100 %, n=12), II (n=12), A (n=6), and B (n=12) in beagle dogs after testing in a crossover design

CYCLOSPORIN COMPOSITIONS AND PROCESS THEREFOR

CROSS-REFERENCE

This is a continuation of Ser. No. 09/605,512, filed Jun. 28, 2000, abandoned, which is a continuation of Ser. No. 09/134,298, filed Aug. 14, 1998, abandoned, which is a continuation of Ser. No. 08/806,106, filed Feb. 25, 1997, abandoned, which is a CIP of PCT/DE95/00951, Jul. 19, 1995.

BACKGROUND OF THE INVENTION

The invention relates to cyclosporin, especially cyclosporin A, containing liquid formulations and soft gelatin capsules for oral administration.

Cyclosporins are neutral cyclic peptides produced by microbes. The most important representative of the cyclosporins is cyclosporin A, which is used in transplant therapy for suppressing organ rejection and in bone marrow transplantation.

Cyclosporin A, its microbiological production, and its isolation and purification to an amorphous, colorless powder is disclosed per se in German Patent 2,455,859.

Cyclosporin A is increasingly also being used in the treatment of autoimmune diseases such as psoriasis, uveitis, nephrotic syndrome and others.

Antiinflammatory and antiparasitic properties are described for the cyclosporins.

Because of the hydrophobic nature of cyclosporin, it is difficult to produce pharmaceutical compositions resulting in high bioavailability of the active ingredient, and there is a very wide inter- and intra-individual variability in the pharmacokinetic parameters. At the same dose, the cyclosporin level in the blood varies by up to 50% from patient to patient. Absorption varies widely even in one and the same patient. However, immunosuppressive therapy relies on a very narrow therapeutic window between dose-dependent side effects and rejection of the transplanted organ.

Poor bioavailabilities are attributable in particular to the low solubility of cyclosporin in the mixture of cyclosporins in dosage forms containing water.

There have thus been very numerous attempts to solve these pharmaceutical problems.

Known and commercially available dosage forms accordingly employ complicated systems of lipophilic and hydrophilic solvents and solubilizing detergents, with the aim of dissolving cyclosporins and keeping them in solution in aqueous systems. They consist of at least four ingredients: namely, active ingredient, vege-table oil, ethanol, and a surfactant.

U.S. Pat. No. 4,388,307 discloses the use of oil and ethanol as vehicle in conjunction with co-solvents. Based on this patent, commercially available drinkable solutions of cyclosporin contain olive oil, ethanol and, as surface-active substance, Labrafil®. This formula entails problems, however. Oils and surface-active vehicles often have an unpleasant odor and/or taste. In addition, oils with unsaturated fatty acids are prone to rancidity.

Secondly, a relatively high content of ethanol is necessary in formulas containing oils. However, this high ethanol content entails difficulties on administration of the products to children and results in storage problems.

When used for filling capsules it is necessary, for the purpose of preventing evaporation, to increase the elaboration of finishing by packaging in aluminium blister packs.

Newer dosage forms disclosed in GB Patent 2,222,770 comprise routes to solutions by the production of micro-emulsions. These systems consist of 4 to 6 components which form a complicated system of active ingredient, lipophilic, hydrophilic phase, and a surface-active substance. Systems of this type entail an increased risk of cross-reaction and the risk that one of the substances used is not tolerated by the patient.

German Patent 3,924,207 discloses a process for producing stable aqueous injection solutions for intravenous administration, which can be administered orally, in which a) 1 part by weight of cyclosporin b) 8–13 parts by weight of one or more monoesters of a or of saturated hydroxy fatty acids with polyethylene glycol and c) 1–13 parts by weight of one or more mono- and/or polyhydric alcohols are mixed.

Pharmaceutical forms which can be used orally have not been produced and investigated in this patent. On attempting to produce formulations in the lower concentration ranges, stated by the inventors, of one or more mono- or polyhydric alcohols, no solution which can provide clear dilutions with water, which is essential for good bioavailability of the active ingredient, is obtained.

All commercially obtainable dosage forms contain oily, lipophilic ingredients (corn oil, kernel oil, corn oil mono-, di-, triglycerides) and one or more detergents and mono- or polyhydric alcohols.

It is evident from DE-A 3,843,054 that orthorhombic crystalline forms such as CY-A/X-II and, in particular, CY-A/X-III are particularly suitable for producing pharmaceutical forms. These formulations are said to contain cyclosporin in stable and fine-particle form and/or have better stability or more favorable release characteristics. These forms are preferably for topical dermal or topical ophthalmic use. The process described for producing the solvate-free orthorhombic crystal forms using ultrasound is difficult to implement on the industrial scale.

It is likewise shown that cyclosporin in amorphous form is less suitable for producing dosage forms.

SUMMARY OF THE INVENTION

The problems which have been described have been solved according to the invention by the surprising finding that in cyclosporin dosage forms for oral administration with a simple composition and high bioavailability in the form of drinkable solution or capsules containing:

a) 1.0 part by weight of one or more amorphous cyclosporin(s) as active ingredient;

b) 7.5 to 7.8, preferably 7.7, parts by weight of one or more polyethylene glycol monoesters of saturated $C_{10}$ to $C_{22}$ hydroxy fatty acids, preferably SOLUTOL® HS 15;

c) 0.7 to 0.85, preferably 0.75, part by weight of a monohydric alcohol as co-solvent, preferably ethanol; and d) 0.7 to 0.8, preferably 0.75, part by weight of a polyhydric alcohol as co-solvent, preferably propylene glycol the cyclosporin(s) provide clear solutions, especially in dilutions with water, when these specific ratios of amounts are maintained.

DETAILED DESCRIPTION OF THE INVENTION

With the selection of this specific solvent composition of a plurality of mono- and polyhydric alcohols in conjunction with the use of amorphous cyclosporin, a formulation which can provide clear dilutions with water in all ratios, especially at high concentrations of cyclosporin in the dosage form, has been found.

This was not normally to be assumed because the concentrations of the co-solvent stated in German Patent 3,924,207 does not permit stable aqueous solutions to be produced in the lower concentration range. Only the combination of mono- and polyhydric alcohols in the stated ratio makes it possible to produce solutions which have a high cyclosporin content and which afford solutions which can provide clear dilutions with water. It is furthermore essential for the possibility of providing clear dilutions with water that the ratio of the monohydric alcohol to the polyethylene glycol monoester is maintained and that the formula contains both mono- and polyhydric alcohols.

It was, therefore, all the more surprising that such a formula showed a bioequivalence with commercial products (see above).

In particular, it was not predictable that such a simple formula without lipophilic component could achieve such high bioavailabilities.

It has furthermore been found that precisely the use of amorphous cyclosporin in an oral administration form results in particularly good solution properties in formulas with a cyclosporin content >5%, which are also maintained in dilutions with water as stable, clear solution.

The invention, therefore, relates to oral dosage forms which, as drinkable solution or packed in capsules, contain the following ingredients in the following ratios of amounts:
 a) 1.0 part by weight of one or more amorphous cyclosporin(s) as active ingredient;
 b) 7.5 to 7.8, preferably 7.7, parts by weight of one or more polyethylene glycol monoesters of saturated $C_{10}$ to $C_{22}$ hydroxy fatty acids, preferably SOLUTOL® HS 15;
 c) 0.7 to 0.85, preferably 0.75, part by weight of a monohydric alcohol as co-solvent, preferably ethanol; and
 d) 0.7 to 0.8, preferably 0.75, part by weight of a polyhydric alcohol as co-solvent, preferably propylene glycol.

In the production process, which is likewise according to the invention, care must be taken that the ratios of amounts are maintained and that the cyclosporin is initially completely dissolved in ethanol with continuous stirring at room temperature and subsequently, likewise with continuous stirring and at room temperature, propylene glycol and Solutol® HS 15 are added. The solutions produced by this process contain 100 mg/mL active ingredient.

Finishing as drinkable solution or capsules takes place in a known manner, for example in capsules each containing 190 mg, 50 mg, or 25 mg of active ingredient.

The production of the composition according to the invention is explained in detail in the following examples:

EXAMPLE 1

100 g of amorphous cyclosporin A are dissolved in 95 mL of ethanol with stirring at room temperature. Subsequently, while stirring further at room temperature, 72 mL of propylene glycol are added. After a clear solution of cyclosporin A has been obtained, 770 g of Solutol® HS 15 are added with further stirring. A clear, viscous solution containing 100 mg/mL cyclosporin A results.

EXAMPLE 2

A cyclosporin A solution produced as in Example 1 is diluted in the ratio 1:40 with water. The resulting solution remains clear and stable over several months.

EXAMPLE 3

Drinkable Solution A
FORMULA:
 cyclosporin A, 5.00 g
 ethanol 96%, 3.75 g
 propylene glycol 3.75 g
 Solutol® HS 15 ad 50.0 mL=38.39 g.

Production takes place by dissolving the cyclosporin in the ethanol, adding propylene glycol, inducing and adding ⅔ of the molten Solutol® and homogenizing. The volume is subsequently made up to 50.0 mL with Solutol®, and homogenization is repeated.

EXAMPLE 4

Drinkable Solution B
FORMULA:
 cyclosporin A, 10.0 g
 propylene glycol 7.5 g
 Solutol® HS 15 77.0 g
 ethanol 96% ad 100 mL=8.18 g
 Production:
  10.0 g of cyclosporin are dissolved in 5 g of ethanol and 7.5 g of propylene glycol, and 77.0 g of Solutol® in the molten state are added. The solution is homogenized and equilibrated at about 25° C. The volume is subsequently made up to 100 mL with ethanol and homogenization is repeated.

EXAMPLE 5

The formulations obtained in accordance with Examples 3 and 4 were tested for bioavailability in beagle dogs compared with products I and II available on the market.

Beagle dogs are regarded as a predictive model for humans for the pharmacokinetics and bioavailability of cyclosporins (compare Ritschel et aL., Meth. and Find. Exp. Clin. Pharmakol. 1989, 11(4):281–287).

The results demonstrate a comparable or better relative bioavailability of the drinkable solutions A and B according to the invention compared with comparative products I and II, while the production is considerably simpler.

BRIEF DESCRIPTION OF THE DRAWING

The relative bioavailability (area under the plasma concentration-time curves) of drinkable solutions a and b is depicted in FIG. 1 compared with the commercially available comparative products I (reference value=100%) and II.

Figure 1:
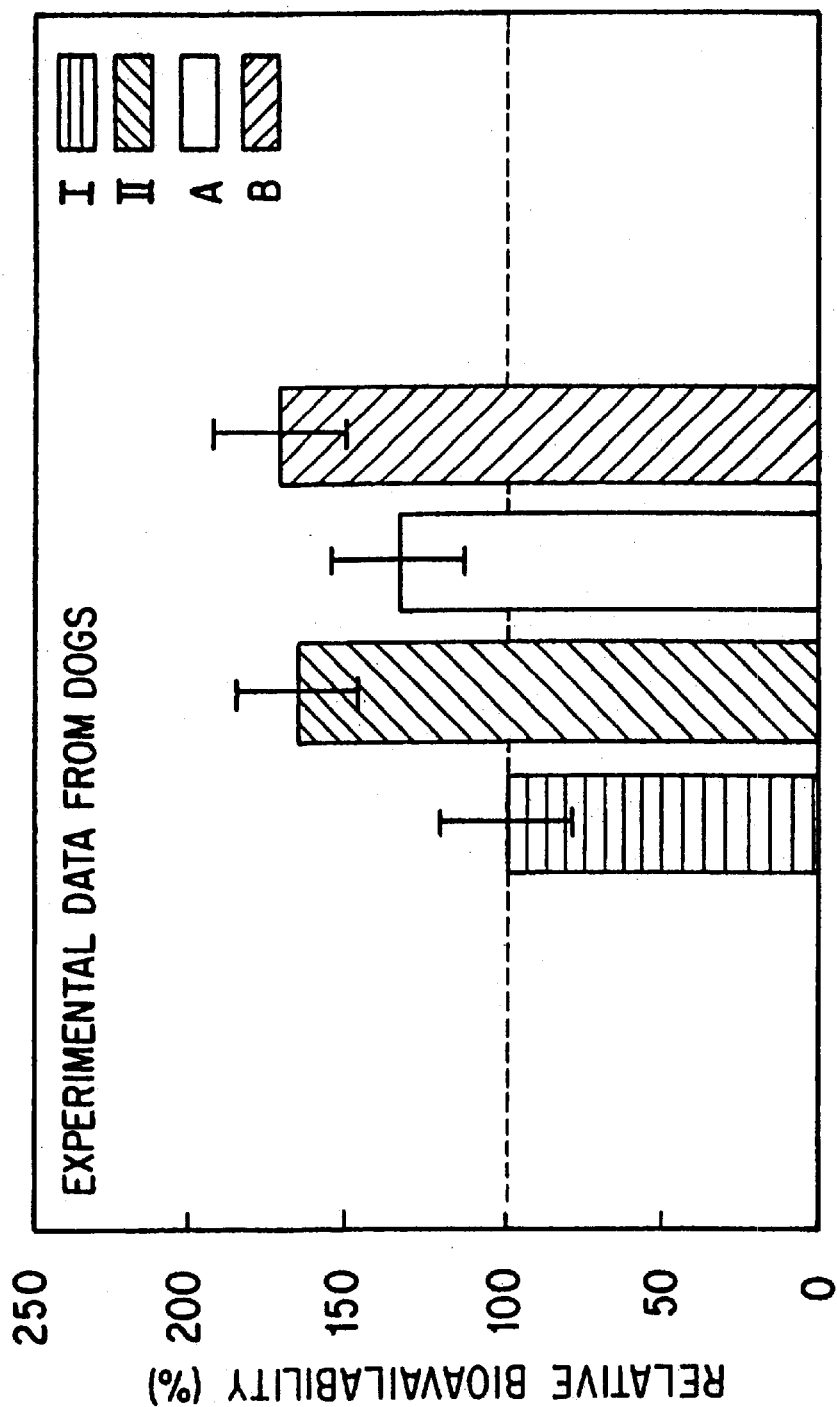

What is claimed is:
1. A formulation comprising:
 a) about 1 part by weight cyclosporin;
 b) 7.5 to 7.8 parts by weight of a polyethylene glycol monoester of a saturated $C_{10}$–$C_{22}$ hydroxy fatty acid;
 c) 0.7 to 0.85 part by weight of a monohydric alcohol as co-solvent; and
 d) 0.7 to 0.8 part by weight of a polyhydric alcohol as co-solvent.
2. A formulation of claim 1 comprising:
 a) about 1 part by weight cyclosporin;
 b) 7.7 parts by weight SOLUTOL® HS 15;
 c) 0.75 part by weight ethanol; and
 d) 0.75 part by weight propylene glycol.
3. A drinkable solution comprising a formulation of claim 2.

4. A method of orally administering a solution of claim 3 to a person in need thereof.

5. A capsule containing a formulation of claim 2.

6. A soft gel capsule of claim 5.

7. A formulation of claim 1 wherein the cyclosporin is amorphous cyclosporin A or amorphous cyclosporin G.

8. A formulation of claim 1 further comprising water.

9. A formulation of claim 1 further comprising water in the ratio cyclosporin to water of from 1 to about 40.

10. A drinkable solution comprising a formulation of claim 1.

11. A method of orally administering a solution of claim 10 to a person in need thereof.

12. A capsule containing a formulation of claim 1.

13. A soft gel capsule of claim 6.

14. A process for the production of a clear cyclosporin solution comprising:

a) dissolving about 1 part by weight cyclosporin in from 0.7 to 0.85 part by weight of a monohydric alcohol as co-solvent with continuous stirring at room temperature; and b) adding from 0.7 to 0.8 part by weight of a polyhydric alcohol as co-solvent and from 7.5 to 7.8 parts by weight of a polyethylene glycol monoester of saturated $C_{10}$–$C_{22}$ hydroxy fatty acid with continuous stirring at room temperature.

15. A process of claim 14 wherein the cyclosporin is cyclosporin A.

16. A process of claim 14 wherein the monhydric alcohol is ethanol and the polyhydric alcohol is propylene glycol.

17. A process of claim 14 wherein the cyclosporin is amorphous cyclosporin A or amorphous cyclosporin G.

* * * * *